(12) United States Patent
Sternlight

(10) Patent No.: US 9,572,718 B2
(45) Date of Patent: Feb. 21, 2017

(54) EYE MASK

(71) Applicant: Cabeau, Inc., Woodland Hills, CA (US)

(72) Inventor: David Bret Sternlight, Canoga Park, CA (US)

(73) Assignee: CABEAU, INC., Woodland Hills, CA (US)

( * ) Notice: Subject to any disclaimer, the term of this patent is extended or adjusted under 35 U.S.C. 154(b) by 0 days.

(21) Appl. No.: 13/959,615

(22) Filed: Aug. 5, 2013

(65) Prior Publication Data

US 2014/0041091 A1    Feb. 13, 2014

Related U.S. Application Data

(60) Provisional application No. 61/680,277, filed on Aug. 7, 2012.

(51) Int. Cl.
| | | |
|---|---|---|
| *A61F 9/04* | (2006.01) | |
| *A61F 11/12* | (2006.01) | |
| *B60N 2/48* | (2006.01) | |
| *A47C 7/38* | (2006.01) | |

(52) U.S. Cl.
CPC .............. *A61F 9/04* (2013.01); *A47C 7/383* (2013.01); *A61F 11/12* (2013.01); *B60N 2/4879* (2013.01); *B60N 2/4882* (2013.01)

(58) Field of Classification Search
CPC .............. A61F 9/04; A61F 9/045; A61F 9/02; A61F 9/026; A61F 13/124; A61F 11/12; A47C 7/383; A41D 13/1184
USPC ... 2/15, 11, 426, 428, 440, 446, 12; 128/858
See application file for complete search history.

(56) References Cited

U.S. PATENT DOCUMENTS

| | | | | |
|---|---|---|---|---|
| 1,743,801 A | * | 1/1930 | Reynolds | 2/15 |
| 2,191,937 A | * | 2/1940 | Low | 2/12 |
| 2,388,635 A | * | 11/1945 | Ditto | 2/441 |
| 2,537,768 A | * | 1/1951 | Laporte | 2/15 |

(Continued)

FOREIGN PATENT DOCUMENTS

| | | |
|---|---|---|
| CN | 1729033 A | 2/2006 |
| CN | 201200086 Y | 3/2009 |

(Continued)

OTHER PUBLICATIONS

International Patent Application and Search Report from corresponding Appl. No. PCT/US2013/053872, dated Feb. 13, 2014.

(Continued)

*Primary Examiner* — Amy Vanatta
(74) *Attorney, Agent, or Firm* — Koppel, Patrick, Heybl & Philpott

(57) ABSTRACT

An eye mask for a person includes a forward portion adapted to cover the person's eyes and having a malleable nose bridge, and two side straps each fixed with the forward portion and terminating at strap ends each having at least one part of a first two-part mechanical fastener. At least one of the side straps may include a first part of a second two-part mechanical fastener for attachment to a seat retention strap adapted to encircle a portion of a seat. Other adjustable attachment means that include a plurality of different straps for encircling the seat or headrest of a seat are included for retaining the person's head against the seat. Each side strap may include a pocket formed therein for holding an ear plug.

38 Claims, 5 Drawing Sheets

(56) References Cited

U.S. PATENT DOCUMENTS

| | | | |
|---|---|---|---|
| 2,543,104 A * | 2/1951 | Golding | A61F 9/04 2/15 |
| 2,582,345 A * | 1/1952 | Moeller | 351/44 |
| 2,671,898 A * | 3/1954 | Wade | A61F 9/027 128/858 |
| 2,726,714 A | 12/1955 | McAndrews | |
| 4,122,847 A * | 10/1978 | Craig | A61F 9/04 128/858 |
| 4,243,041 A * | 1/1981 | Paul | 607/109 |
| 4,365,354 A | 12/1982 | Sullivan | |
| 4,707,031 A | 11/1987 | Meistrell | |
| 4,797,956 A * | 1/1989 | Boyce | A61F 9/025 128/206.19 |
| D302,167 S | 7/1989 | Sherman | |
| 4,858,609 A | 8/1989 | Cole | |
| 4,872,217 A | 10/1989 | Kitayama | |
| 5,425,380 A * | 6/1995 | Hudson et al. | 128/858 |
| 5,700,238 A * | 12/1997 | Hyson | 602/74 |
| 5,940,886 A | 8/1999 | McCarthy Smith | |
| 6,067,664 A | 5/2000 | Cortes | |
| D465,234 S | 11/2002 | Gordon | |
| 6,607,245 B1 | 8/2003 | Scher | |
| D489,749 S | 5/2004 | Landvik | |
| 6,745,397 B2 * | 6/2004 | Magidson | 2/15 |
| 7,202,774 B2 | 4/2007 | Hoyle | |
| D592,236 S * | 5/2009 | McGrath | D16/301 |
| D615,453 S | 5/2010 | Spears | |
| 7,721,350 B1 * | 5/2010 | Eaton | 2/15 |
| 7,832,802 B2 | 11/2010 | Ehlers et al. | |
| 8,662,590 B2 | 3/2014 | Bogen | |
| 2003/0079266 A1 * | 5/2003 | Magidson | A61F 9/045 2/15 |
| 2005/0046549 A1 | 3/2005 | Hoyle | |
| 2009/0090364 A1 | 4/2009 | Daugaard et al. | |
| 2009/0255026 A1 * | 10/2009 | Benner | 2/12 |
| 2010/0122398 A1 * | 5/2010 | Luciano | 2/173 |
| 2012/0222185 A1 * | 9/2012 | Erikson | A61F 9/04 2/11 |

FOREIGN PATENT DOCUMENTS

| | | |
|---|---|---|
| CN | 201500227 U | 6/2010 |
| CN | 101820951 A | 9/2010 |
| DE | 102006054880 A1 * | 5/2008 |
| RU | 38094 U1 | 5/2004 |
| RU | 2348389 C2 | 10/2009 |
| WO | WO 2007045041 A1 | 4/2007 |
| WO | 2010076707 A1 | 8/2010 |

OTHER PUBLICATIONS

International Preliminary Report on Patentability from corresponding PCT application No. PCT/US2013/053872, dated Feb. 19, 2015.
Extended European Search Report from application No. 13827065.7, dated Mar. 1, 2016.
First Office Action from corresponding Chinese Patent Appl, No. 2013800417136, dated Dec. 30, 2015.
Second Office Action from Chinese Patent Appl. No. 2013800417136, dated Nov. 1, 2016.

* cited by examiner

EYE MASK

CROSS-REFERENCE TO RELATED APPLICATIONS

This application claims the benefit of U.S. Provisional Patent Application 61/680,277, filed on Aug. 7, 2012, and incorporated herein by reference.

STATEMENT REGARDING FEDERALLY SPONSORED RESEARCH AND DEVELOPMENT

Not Applicable.

FIELD OF THE INVENTION

This invention relates to eye masks, and more particularly to an eye mask for travelers.

DISCUSSION OF RELATED ART

Currently, there are many eye masks, eye pillows, sleep masks, and the like available for assisting people in sleeping, resting, relaxing, or meditating by blocking light to their eyes. With such prior art devices, light often seeps in from the top or, more commonly, from the bottom of the device, as such prior devices are not form-fitting to each person's facial features. These areas of the face often differ, in some cases dramatically, from person to person, making a one-size-fits-all approach unsatisfactory for many consumers. In some environments, such as in bed, in a chair such as at home or an office, or on a seat of an airplane, train, bus, or car, or in any potentially bright area, such light penetrating to the eyes may prevent one from either falling or staying asleep.

For example, U.S. Pat. No. 4,872,217 to Kitayama on Oct. 10, 1989 teaches an eye mask that has a specific fixed shape around the nose. As this nose bridge area is not adaptable to people having different sizes or shapes of noses and cheek bones, in many cases ambient light may seep in between the mask and the user's face.

U.S. Pat. No. D302,167 to Sherman on Jul. 11, 1989 teaches an eye mask with an apparently pliable internal perimeter that requires apparently elastic straps to hold the mask onto the face. Such elastic straps apply a pressure against the face that is uncomfortable to many users and can result in a claustrophobic feeling of pressure against the face.

U.S. Pat. No. D465,234 to Gordon on Nov. 5, 2002 and U.S. Pat. No. D489,749 to Landvik on May 11, 2004 both teach eye masks that appears to be deformable around the nose area and presumably fixes with a hook-and-loop type fastener around the back of the user's head. Such devices are relatively large on the head and as such are relatively heavy, hot and uncomfortable.

Many people utilize a U-shaped neck pillow or so-called travel pillow when traveling and trying to sleep in an upright position. With such prior art devices, if one does manage to fall asleep while sitting upright, often his head will drop down suddenly, waking the person up in an unrestful cyclic process. Such prior art devices fail to maintain one's head held back against the seat while the user sleeps, and provide little lateral support.

Heretofore there hasn't been an adequate solution to maintain a sleeper's head against a seat while simultaneously providing an improved eye mask for keeping ambient light out of a user's eyes.

Therefore, there is a need for a device that maintain a sleeper's head against a seat while simultaneously providing an improved eye mask for keeping ambient light out of a user's eyes. Such a needed invention would further provide for attenuating ambient noise from the user's ears, and would be an attractive, minimal size. Such a needed device would be adaptable to a variety of vehicle seats, and would allow shaping to match the particular shape of a user's face and nose. The present invention accomplishes these objectives.

SUMMARY OF THE INVENTION

The present device is an eye mask for a person that includes a forward portion adapted to cover the person's eyes. Preferably the forward portion includes a malleable nose bridge for conforming to the person's nose. The forward portion may comprise an opaque outer layer and an inner malleable layer.

In one embodiment, the opaque outer layer includes a pair of eye depressions, such that the person's eyelids and eye lashes do not contact the outer layer when the eye mask is worn by the person. Further, the eye mask may include at least one padded area on an inside surface thereof.

Two side straps are each fixed with the forward portion and terminate at strap ends. Each strap end has at least one part of a first two-part mechanical fastener, such as a hook-and-loop type fastener. As such, the eye mask may be secured to the person's head by mutually fastening each part of the first two-part mechanical fastener.

In one embodiment, at least one of the side straps includes a pocket adapted to hold at least one ear plug, or the like. In an embodiment wherein each of the two side straps includes one of the pockets, each pocket may include one of the ear plugs fixed thereto with a tether to reduce the chance of the ear plugs from being misplaced.

In use, with the strap ends mutually fixed with the mechanical fastener around the person's head, the forward portion shields ambient light from the person's eyes. The malleable nose bridge may be adjusted to conform to the person's nose and face to further shield ambient light from the person's eyes.

At least one of the side straps may include a first part of a second two-part mechanical fastener, such as a hook and loop-type fastener, a pair of magnets, or the like. In such an embodiment, the eye mask further includes a seat retention strap adapted to encircle a portion of a seat, such as an existing airline or automotive seat. Such a seat retention strap includes at least one length adjustment buckle and a second part of the second two-part mechanical fastener and optionally a fastening two-part buckle for securing ends of the retention strap mutually together. Each length adjustment buckle may include a cam-lock mechanism to selectively secure the strap therein.

As such, the seat retention strap is fixed around the portion of the seat and secured thereto by mutually fastening each strap end together and adjusting the length adjustment buckle. With the second part of the second two-part mechanical fastener facing forward, and with the eye mask worn by the person with the first part of the second two-part mechanical fastener facing rearward, the first and second parts, of the second two-part mechanical fastener may be mutually fastened to retain the person's head against the seat.

Alternately, each side strap may further include a first part of a third mechanical fastener adapted to be selectively fixed with a retention strap that terminates at ends thereof with a second part of the third mechanical fastener. Such a third mechanical fastener may include a pair of magnets, a ring and a mechanical clips, or the like. As such, the retention strap may be fixed around the seat and fixed with each side strap to retain the person's head against the seat. The retention strap may include one of the length adjustment buckles.

The retention strap may comprise a seat retention strap adapted to encircle the portion of a seat and including one of the length adjustment buckles. The retention strap may further include a pair of forward retention straps each terminating at a forward end thereof with one of the second parts of the third mechanical fastener, and each terminating at a rearward end with a strap connector adapted to selectively secure the forward retention strap with the seat retention strap. Each forward retention strap may further include one of the length adjustment buckles, such that the length of the forward retention strap may be selectively adjustable.

As such, the seat retention strap may be fixed about the portion of the seat and secured thereto by adjusting the length of the seat retention strap with its length adjustment buckle. Each forward retention strap is fixed at its rearward end with the seat retention strap and at its forward end with one of the side straps. As such, with the eye mask worn by the person, the person's head is retained in a generally fixed position against the seat.

The present invention maintains a sleeper's head against a seat while simultaneously providing an improved eye mask for keeping ambient light out of a user's eyes. The present device further provides for attenuating ambient noise from the user's ears, and takes an attractive, minimal size. Further, the present invention is adaptable to a variety of vehicle seats, and allows shaping to match the particular shape of a user's face and nose. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
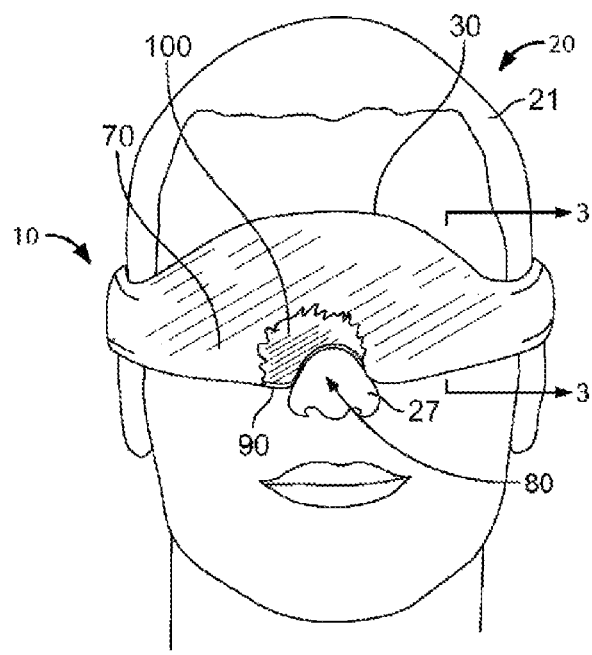
FIG. 1 is a front perspective view of one embodiment of the invention.
Figure 2:
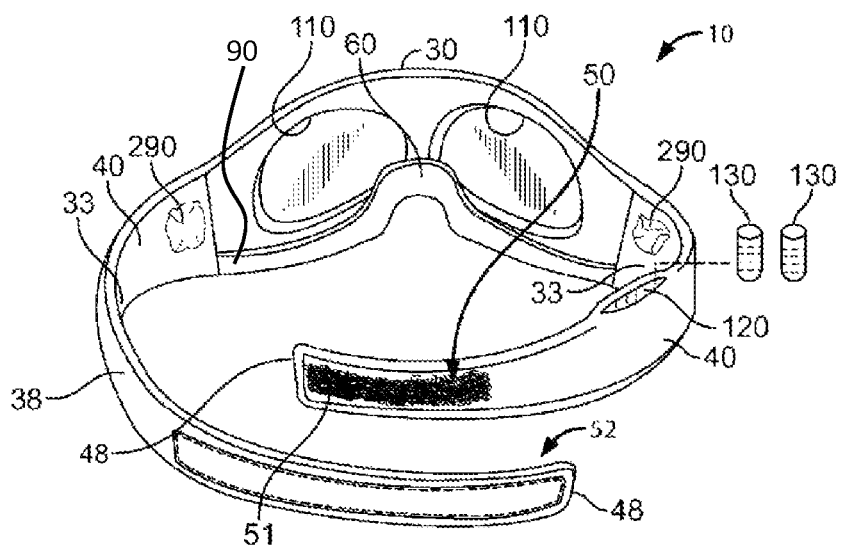
FIG. 2 is a rear perspective view of one embodiment of the invention.

FIGS. 1 and 2 illustrate an eye mask 10 for a person 20. A forward portion 30 of the eye mask 10 is adapted to cover the person's eyes 22. Preferably the forward portion 30 includes a malleable nose bridge 60 for conforming to the person's nose 27. The forward portion 30 may comprise an opaque outer layer 70 and an inner malleable layer 80. In such an embodiment, the malleable layer 80 forms the malleable nose bridge 60 and comprises a flexible outer sheath 90 surrounding an internal malleable material 100 (FIG. 3), such as a metal material.

Figure 4:
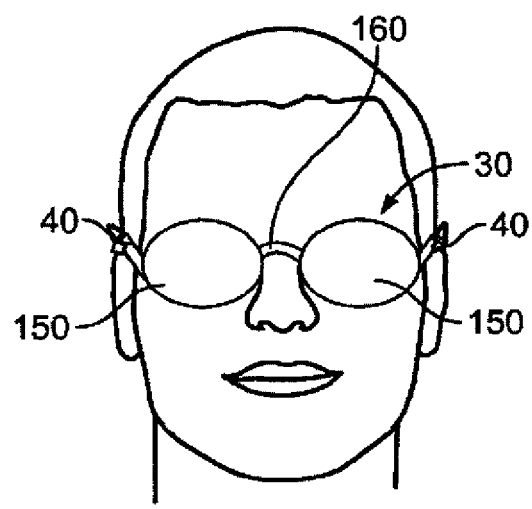
FIG. 4 is a left-side elevational view of an alternate embodiment of the invention.

In one embodiment, illustrated in FIG. 4, the forward portion 30 takes the shape of a pair of eyeglasses that includes a pair of lens-looking sections 150 fixed together at a nose bridge 160. The forward portion 30 is preferably made with a flexible polyester fabric material, but can be made of any suitably opaque and flexible material that is soft against the person's skin.

Figure 3:
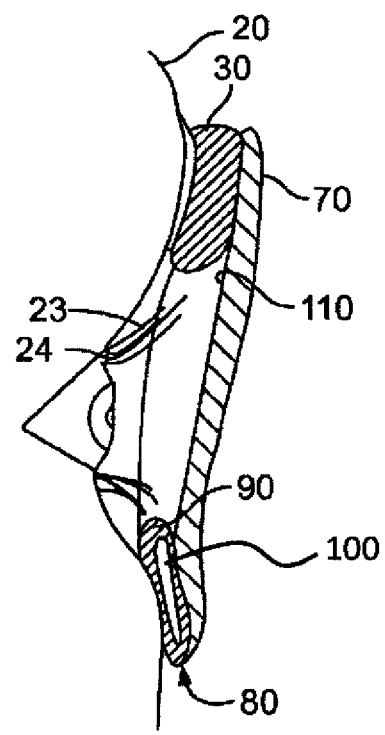
FIG. 3 is a partial cross-sectional view of the invention, taken generally along lines 3-3 of FIG. 1.

In one embodiment, the opaque outer layer includes a pair of eye depressions 110, such that the person's eyelids 24 and eye lashes 23 do not contact the outer layer 70 when the eye mask 10 is worn by the person 20 (FIG. 3). Further, the eye mask 10 may include at least one padded area 290 on an inside surface 33 thereof (FIG. 2).

Two side straps 40 are each fixed with the forward portion 30 and terminate at strap ends 48. Each strap end 48 has at least one part 51,52 of a first two-part mechanical fastener 50, such as a hook-and-loop type fastener 50. Each side strap 40 may be made with a tricot or Terylene material, which also acts as a loop portion 51 of a hook-and-loop type fastener 50. As such, the eye mask 10 may be secured to the person's head 21 by mutually fastening each part 51,52 of the first two-part mechanical fastener 50.

In one embodiment (not shown) the eye mask 10 is reversible, with an inside surface 33 of the eye mask 10 having a different-looking material than an outside surface 37. As such, both strap ends 48 have at least one part 51,52 of the first two-part mechanical fastener 50 on both an inside surface 33 and an outside surface 38 thereof.

Figure 6:
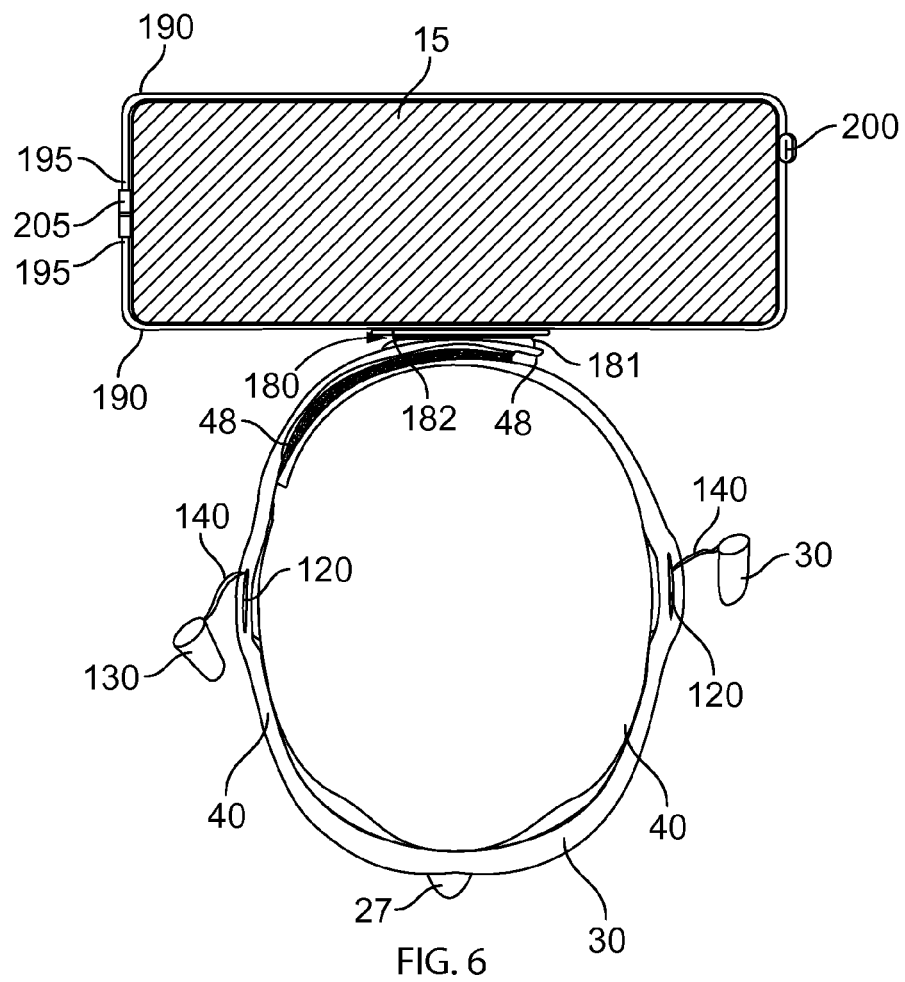
FIG. 6 is a top plan view of an embodiment of the invention having a seat retention strap.

In one embodiment, at least one of the side straps 40 includes a pocket 120 adapted to hold at least one ear plug 130, or other item. In an embodiment wherein each of the two side straps 40 includes one of the pockets 120, each pocket 120 may include one of the ear plugs 130 fixed thereto with a tether 140 to reduce the chance of the ear plugs 130 from being misplaced (FIGS. 2 and 6).

Figure 5:
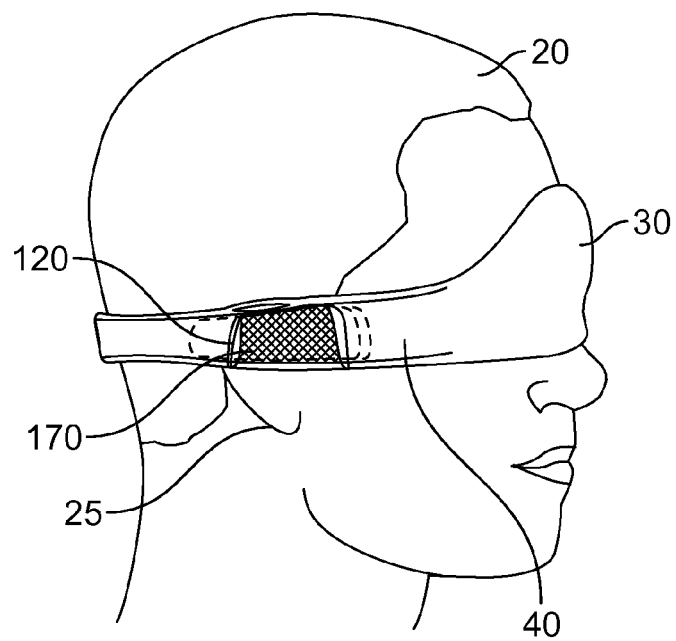
FIG. 5 is a front elevational view of another alternate embodiment of the invention.

Each side strap 40 may further include an elastic portion 170 proximate the person's ear 25 when worn by the person 20 (FIG. 5). The elastic portion 170 is deformable by the person's ear 25 to reduce tension on the person's ear 25 by the side strap 40. Each elastic portion 170 may form the pocket 120 adapted to hold at least one ear plug 130. Each elastic portion 170 may extend downwardly to cover substantially all of the person's ear 25, and may include a dense, inner layer (not shown) that attenuates sound when rolled down over the person's ear 25.

In use, with the strap ends 48 mutually fixed with the mechanical fastener 50 around the person's head, the forward portion 30 shields ambient light from the person's eyes 22. The malleable nose bridge 60 may be adjusted to conform to the person's nose 27 and face to further shield ambient light from the person's eyes 22.

At least one of the side straps 40 may include a first part 181 of a second two-part mechanical fastener 180 (FIG. 6), such as a hook and loop-type fastener, a pair of magnets, or the like. In such an embodiment, the eye mask 10 further includes a seat retention strap 190 adapted to encircle a portion of a seat 15, such as an existing airline or automotive seat 15. Such a seat retention strap 190 includes at least one length adjustment buckle 200 and a second part 182 of the second two-part mechanical fastener 180 and optionally a fastening two-part buckle 205 for securing ends 195 of the retention strap 190 mutually together. Each length adjustment buckle 200 may include a cam-lock mechanism to selectively secure the strap 190 therein.

As such, the seat retention strap 190 is fixed around the portion of the seat 15 and secured thereto by mutually fastening each strap end 195 together and adjusting the length adjustment buckle 200. With the second part 182 of the second two-part mechanical fastener 180 facing forward, and with the eye mask 10 worn by the person 20 with the first part 181 of the second two-part mechanical fastener 180 facing rearward, the first and second parts 181,182 of the second two-part mechanical fastener 180 may be mutually fastened to retain the person's head 21 against the seat 15.

Figure 7:
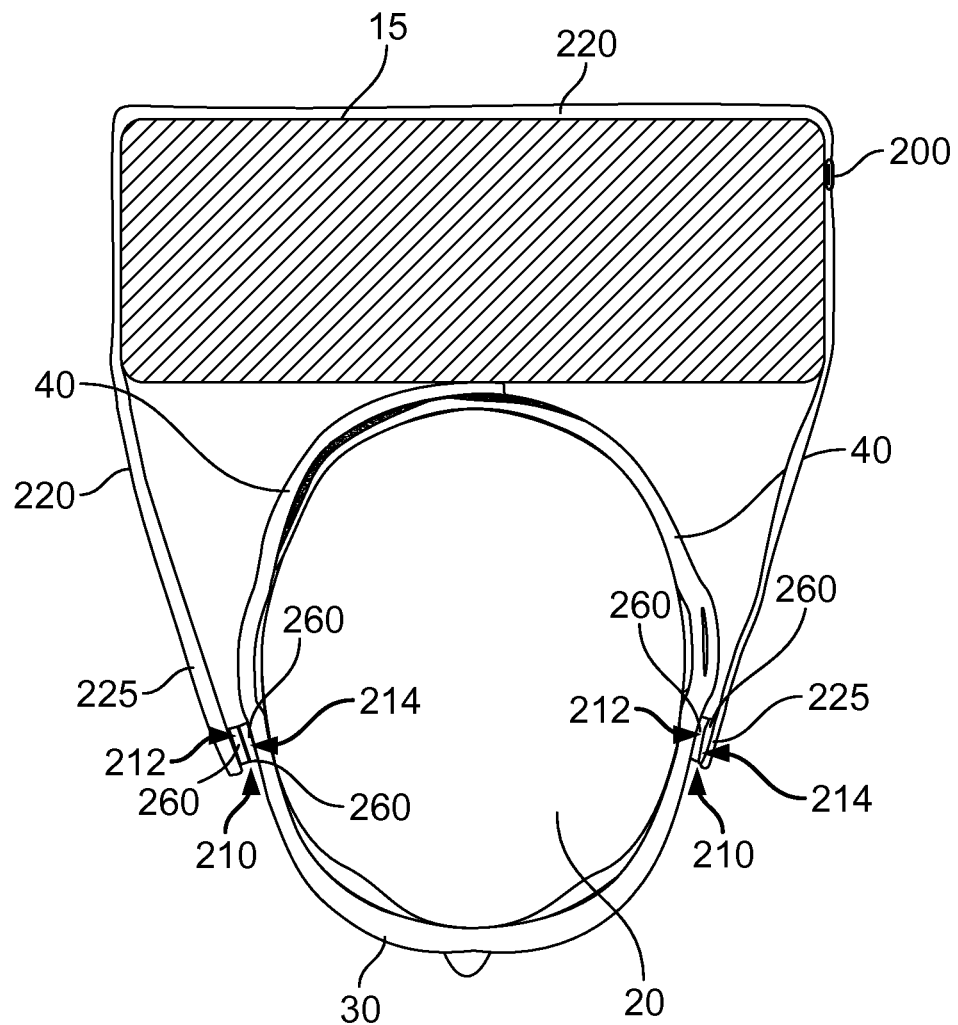
FIG. 7 is a top plan view of an alternate embodiment of the invention having a retention strap.

Each side strap 40 may further include a first part 212 of a third mechanical fastener 210 adapted to be selectively fixed with a retention strap 220 that terminates at ends 25 thereof with a second part 214 of the third mechanical fastener 210 (FIG. 7). Such a third mechanical fastener 210 may include a pair of magnets 260 (FIG. 7), a ring 270 and a mechanical clips 280 (FIG. 8), or the like. As such, the retention strap 220 may be fixed around the seat 15 and fixed with each side strap 40 to retain the person's head 21 against the seat 15. The retention strap 220 may include one of the length adjustment buckles 200.

Figure 8:
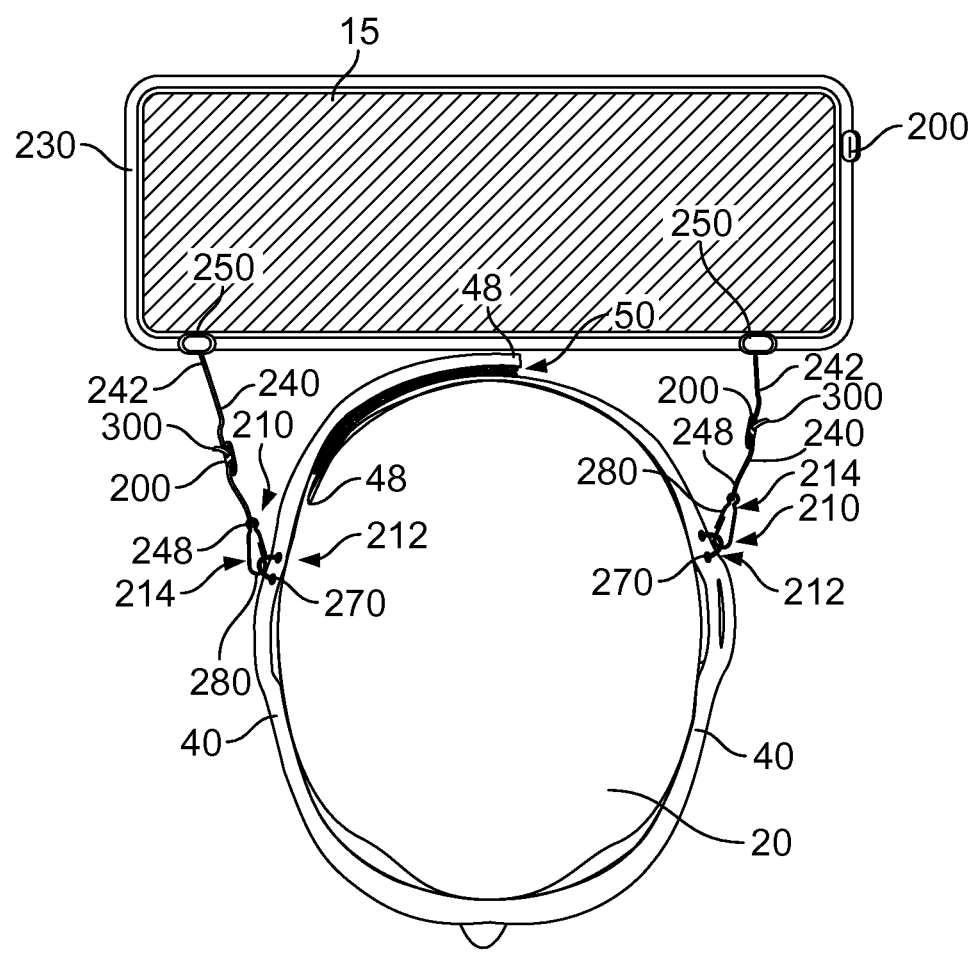
FIG. 8 is a top plan view of an embodiment of the invention having a seat retention strap that includes a seat retention strap and a pair of forward retention straps.

The retention strap 220 may comprise a seat retention strap 230 adapted to encircle the portion of a seat 15 and including one of the length adjustment buckles 200. The retention strap 200 may further include a pair of forward retention straps 240 each terminating at a forward end 248 thereof with one of the second parts 214 of the third mechanical fastener 210, and each terminating at a rearward end 242 with a strap connector 250 adapted to selectively secure the forward retention strap 240 with the seat retention strap 230 (FIG. 8). Each forward retention strap 240 may further include one of the length adjustment buckles 200, such that the length of the forward retention strap 240 may be selectively adjustable.

As such, the seat retention strap 230 may be fixed about the portion of the seat 15 and secured thereto by adjusting the length of the seat retention strap 230 with its length adjustment buckle 200. Each forward retention strap 240 is fixed at its rearward end 242 with the seat retention strap 230 and at its forward end 248 with one of the side straps 40.

As such, with the eye mask 10 worn by the person 20, the person's head 21 is retained in a generally fixed position against the seat 15.

Each strap 190,220,240 is preferably made from a flexible nylon strap material, or the like. Further, each length adjustment buckle 200, strap connector 250, and cam lock mechanism 300 is preferably made from a rigid plastic molded material.

While a particular form of the invention has been illustrated and described, it will be apparent that various modifications can be made without departing from the spirit and scope of the invention. For example, the shapes for the forward portion 30 and the side straps 40 as illustrated in the drawings show certain embodiments that may look different than other embodiments that are still covered by the scope of the appended claims. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. An eye mask for a person, comprising:
   a forward portion configured to cover a person's eyes, said forward portion comprising:
   a main body; and
   an elongated malleable layer along an inside surface of said main body, said elongated malleable layer shaped to define a nose bridge and comprising:
   an elongated outer sheath on said inside surface of said main body; and
   an internal malleable material within said elongated outer sheath for conforming to a person's nose, said internal malleable material able to be pressed permanently out of shape;
   wherein said main body is shaped to define two eye depressions; and
   wherein said elongated outer sheath is attached to said inside surface of said main body entirely below said two eye depressions.

2. The eye mask of claim 1, wherein said main body comprises an opaque outer layer;
   wherein said opaque outer layer is shaped to define two eye depressions.

3. The eye mask of claim 1, further comprising a head strap;
   wherein said head strap comprises a pocket configured to hold an ear plug.

4. The eye mask of claim 1, further comprising a head strap;
   wherein an inner surface of said head strap comprises a padded area.

5. The eye mask of claim 1, further comprising first and second side straps;
   wherein said first side strap comprises a first mechanical fastener and said second side strap comprises a second mechanical fastener configured to connect to said first mechanical fastener.

6. The eye mask of claim 5, wherein said first and second mechanical fasteners are configured to form a hook-and-loop type fastener.

7. The eye mask of claim 1, wherein said elongated malleable layer extends past each of said two eye depressions.

8. The eye mask of claim 7, wherein said elongated malleable layer at least partially defines each of said two eye depressions.

9. The eye mask of claim 7, wherein said elongated malleable layer at least partially defines a bottom portion of each of said two eye depressions.

10. The eye mask of claim 1, wherein said internal malleable material comprises metal.

11. The eye mask of claim 1, wherein said elongated malleable layer is substantially tubular.

12. The eye mask of claim 1, wherein said elongated malleable layer is along a bottom edge of said inside surface of said main body.

13. The eye mask of claim 12, wherein said elongated malleable layer covers less than all of said inside surface of said main body.

14. The eye mask of claim 1, wherein said elongated malleable layer covers less than half of said inside surface of said main body.

15. The eye mask of claim 1, wherein said elongated malleable layer has a height substantially smaller than the height of said main body.

16. The eye mask of claim 1, wherein said elongated malleable layer is below said two eye depressions.

17. An eye mask for a person, comprising:
    a forward portion configured to cover a person's eyes and shaped to define two eye depressions, said forward portion comprising:
    a main body;
    an elongated outer sheath; and
    an internal malleable material within said outer sheath for conforming to a person's nose;
    wherein said elongated outer sheath extends below and past each of said two eye depressions; and
    wherein said elongated outer sheath is on less than all of an inside surface of said main body.

18. The eye mask of claim 17, wherein said forward portion comprises left and right ends;
    wherein said elongated outer sheath extends to said left and right ends.

19. The eye mask of claim 18, further comprising a strap attached to one or both of said left and right ends.

20. The eye mask of claim 17, wherein said two eye depressions and said elongated outer sheath are on a same side of said forward portion.

21. The eye mask of claim 17, wherein said elongated outer sheath at least partially defines each of said two eye depressions.

22. The eye mask of claim 17, wherein said elongated outer sheath at least partially defines a bottom portion of each of said two eye depressions.

23. The eye mask of claim 17, wherein said internal malleable material is able to be pressed permanently out of shape.

24. The eye mask of claim 17, wherein said internal malleable material comprises metal.

25. The eye mask of claim 17, wherein said elongated outer sheath extends below and past a lower edge of each of said two eye depressions.

26. The eye mask of claim 17, wherein said elongated outer sheath has a height substantially smaller than the height of said forward portion.

27. The eye mask of claim 17, wherein said elongated outer sheath is on less than half of said inside surface of said main body.

28. The eye mask of claim 17, wherein said elongated outer sheath is attached to said inside surface between a lower edge of each of said two eye depressions and a bottom of said inside surface of said main body.

29. An eye mask, comprising:
    a main body comprising a front surface and a back surface, wherein said back surface is shaped to define two eye depressions;
    an elongated outer sheath on a lower portion of said back surface of said main body;
    an internal malleable material within said outer sheath, said internal malleable material comprising metal;
    wherein portions of said front surface corresponding to said two eye depressions are substantially flat.

30. The eye mask of claim 29, wherein said elongated outer sheath is on less than all of said back surface of said main body.

31. The eye mask of claim 29, wherein said elongated outer sheath is on less than half of said back surface of said main body.

32. The eye mask of claim 29, wherein said elongated outer sheath extends along a bottom edge of said back surface of said main body.

33. The eye mask of claim 29, wherein said elongated outer sheath extends below and past each of said two eye depressions.

34. The eye mask of claim 29, wherein said front surface is substantially flat.

35. The eye mask of claim 29, wherein said internal malleable material is configured to conform to a user's nose and cheeks.

36. The eye mask of claim 29, wherein elongated outer sheath has a height substantially smaller than the height of said main body.

37. An eye mask, comprising:
- a main body comprising a front surface and a back surface, wherein said back surface is shaped to define two eye depressions;
- an elongated outer sheath on a lower portion of said back surface of said main body;
- an internal malleable material within said outer sheath, said internal malleable material comprising metal;
- wherein said elongated sheath is on less than all of said back surface of said main body.

38. The eye mask of claim 37, wherein said elongated outer sheath is on less than half of said back surface of said main body.

* * * * *